United States Patent
Fox et al.

(10) Patent No.: US 9,534,493 B2
(45) Date of Patent: Jan. 3, 2017

(54) PRESSURE MEASUREMENT CELL FOR USE IN AN INFUSION OR INJECTION SYSTEM

(71) Applicant: ULRICH GMBH & CO. KG, Ulm (DE)

(72) Inventors: Frederik Fox, Ulm (DE); Uwe Striggow, Ulm (DE); Florian Kolich, Ulm (DE); Daniel Philipp, Ulm (DE)

(73) Assignee: ULRICH GMBH & CO. KG, Ulm (DE)

( * ) Notice: Subject to any disclaimer, the term of this patent is extended or adjusted under 35 U.S.C. 154(b) by 283 days.

(21) Appl. No.: 14/312,753

(22) Filed: Jun. 24, 2014

(65) Prior Publication Data

US 2014/0373618 A1 Dec. 25, 2014

(30) Foreign Application Priority Data

Jun. 24, 2013 (DE) .......................... 10 2013 106 582

(51) Int. Cl.
*B01D 35/02* (2006.01)
*E21B 49/08* (2006.01)
*A61M 5/165* (2006.01)
*A61M 5/168* (2006.01)

(52) U.S. Cl.
CPC ............ *E21B 49/084* (2013.01); *A61M 5/165* (2013.01); *B01D 35/02* (2013.01); *A61M 5/16854* (2013.01); *A61M 2005/1652* (2013.01); *A61M 2205/3327* (2013.01); *A61M 2205/3331* (2013.01); *E21B 2049/085* (2013.01)

(58) Field of Classification Search
CPC .. E21B 49/084; E21B 2049/085; B01D 35/02; A61M 5/165; A61M 5/16854; A61M 2205/3331; A61M 2205/3327; A61M 2005/1652
See application file for complete search history.

(56) References Cited

U.S. PATENT DOCUMENTS

| 3,696,932 | A | * | 10/1972 | Rosenberg | .......... | A61M 1/3627 |
| | | | | | | 210/437 |
| 3,970,084 | A | * | 7/1976 | Raines | .................. | A61M 5/162 |
| | | | | | | 210/445 |
| 3,970,490 | A | * | 7/1976 | Raines | .................. | A61M 5/162 |
| | | | | | | 156/196 |

(Continued)

FOREIGN PATENT DOCUMENTS

| DE | 19900937 | 7/2000 |
| EP | 776469 | 6/1997 |

(Continued)

*Primary Examiner* — David Bolduc
(74) *Attorney, Agent, or Firm* — Paul D. Bianco; Gary S. Winer; Fleit Gibbons Gutman Bongini & Bianco PL (57) ABSTRACT

A pressure measurement cell for use in an infusion or injection system for the injection of a fluid, with a housing in which at least one filter unit, through which the fluid under pressure is conducted, and at least one pressure transducer for the detection of the pressure of the fluid flowing from the filter unit are located. Such a pressure measurement cell is pressure-stable, causes only a slight pressure decline in the hose system of the infusion or injection system, can be produced at low cost, and makes possible a simple installation and handling when the hose system is inserted into a hose pump.

20 Claims, 6 Drawing Sheets

(56) References Cited

U.S. PATENT DOCUMENTS

| | | | | |
|---|---|---|---|---|
| 4,001,929 A * | 1/1977 | Ishikawa | A61M 5/165 | |
| | | | 29/234 | |
| 4,014,797 A * | 3/1977 | Raines | A61M 5/162 | |
| | | | 210/446 | |
| 4,450,078 A * | 5/1984 | Walker | A61M 5/165 | |
| | | | 210/315 | |
| 4,642,098 A * | 2/1987 | Lundquist | A61M 5/165 | |
| | | | 128/DIG. 12 | |
| 5,914,033 A * | 6/1999 | Carlsson | A61M 1/3639 | |
| | | | 210/335 | |
| 6,280,632 B1 * | 8/2001 | Polaschegg | A61M 1/3462 | |
| | | | 210/103 | |
| 6,357,600 B1 * | 3/2002 | Scagliarini | A61M 5/165 | |
| | | | 210/448 | |
| 6,558,125 B1 * | 5/2003 | Futterknecht | A61M 5/16854 | |
| | | | 417/1 | |
| 7,069,788 B2 * | 7/2006 | Teugels | A61M 1/3639 | |
| | | | 73/706 | |
| 7,516,665 B2 * | 4/2009 | Teugels | A61M 1/3639 | |
| | | | 73/706 | |
| 8,065,924 B2 * | 11/2011 | Ziegler | A61M 5/16854 | |
| | | | 73/861.61 | |
| 8,216,184 B2 * | 7/2012 | Balestracci | A61M 5/14 | |
| | | | 604/126 | |
| 8,241,237 B2 * | 8/2012 | Gatti | A61M 1/3639 | |
| | | | 604/27 | |
| 8,317,674 B2 * | 11/2012 | Quirico | G21F 3/00 | |
| | | | 600/5 | |
| 8,708,352 B2 * | 4/2014 | Quirico | A61M 5/007 | |
| | | | 280/47.35 | |
| 9,114,203 B2 * | 8/2015 | Quirico | A61M 5/14 | |
| 9,123,449 B2 * | 9/2015 | Quirico | A61M 5/14 | |
| 2007/0135779 A1 * | 6/2007 | Lalomia | A61M 1/0005 | |
| | | | 604/319 | |
| 2009/0012464 A1 * | 1/2009 | Martin | A61M 5/1418 | |
| | | | 604/82 | |
| 2009/0157040 A1 * | 6/2009 | Jacobson | A61M 5/16804 | |
| | | | 604/505 | |
| 2010/0228222 A1 * | 9/2010 | Williams | A61M 1/0058 | |
| | | | 604/500 | |
| 2010/0274171 A1 * | 10/2010 | Caleffi | A61M 1/3627 | |
| | | | 604/6.09 | |
| 2011/0092920 A1 | 4/2011 | Martin et al. | | |
| 2013/0079632 A1 | 3/2013 | Baecke et al. | | |

FOREIGN PATENT DOCUMENTS

| | | |
|---|---|---|
| EP | 2011541 | 1/2009 |
| WO | 96/05494 | 2/1996 |
| WO | 2011100851 | 8/2011 |

* cited by examiner

PRESSURE MEASUREMENT CELL FOR USE IN AN INFUSION OR INJECTION SYSTEM

CROSS REFERENCE TO RELATED APPLICATION

This application claims priority under 35 U.S.C. §119 to German Patent Application No. 10 2013 106 582.1 filed 24 Jun. 2013, the entire contents of which are incorporated herein by reference.

FIELD OF THE DISCLOSURE

The disclosure concerns a pressure measurement cell for use in an infusion or injection system for the injection of a fluid, wherein the pressure measurement cell comprises a housing, in which at least one filter unit, through which the fluid standing under pressure is conducted, and a pressure transducer, for the detection of the pressure of the pressure of the fluid flowing from the filter unit, are located.

BACKGROUND OF THE DISCLOSURE

In an infusion or injection system for the injection of a liquid, pressure measurement cells are used to detect the pressure of the liquid to be injected; they are located, for example, in an injection hose, in which the liquid is conveyed to an injection cannula. Thus, for example, Offenlegungsschrift DE 19900937 A1 shows an injector for the application of liquids, in particular, contrasting agents for X-ray tomography or magnetic resonance imaging, with a hose and a roller pump, which is at least partially embraced by the hose in a circumferential direction, to convey the liquid from a supply container to a cannula, wherein an opening formed in the hose wall is connected with the pressure chamber, connected, in turn, with the interior of the hose (3); the chamber has a component which can be adjusted by the effect of the liquid pressure and which acts on a pressure sensor.

From the European Patent EP 2011541 B1, a hose system, for an injection for the intravenous injection of contrasting agents and saline solution, is known, with a pump hose that is coupled with a pump, to convey the contrasting agent or the saline solution, in which a pressure sensor or, separately from it, a particle filter are arranged, one behind the other.

The disadvantage with such a system, in which the pressure measurement cell and the particle filter are separated from one another, is the cost factor. Thus, the pressure sensor and the particle filter have their own housing units, which increase the production costs of the system. In addition, the installation of the individual parts is more expensive, since more operations have to be undertaken in assembling the hose system. Another disadvantage is the low pressure stability of the particle filter used, which is usually designed as a pan filter. Also unfavorable is the increased pressure decline between the entry of the filter and its exit from the particle filter, which is produced by the relatively small filter area, which corresponds to the cross section of the pump hose. The handling operations when placing the pump hose into the pump is also disadvantageous.

SUMMARY OF THE DISCLOSURE

In embodiments, the pressure measurement cell for use in an infusion or injection system disclosed can be produced at a lower cost, which makes possible a simple installation, which is as pressure-stable as possible, and causes only a low pressure decline in the hose system of the infusion or injection system, and guarantees as simple as possible a handling when inserting the hose system into a hose pump.

In accordance with the disclosure, a pressure measurement cell has a housing, in which a pressure transducer for the detection of the pressure of the liquid flowing through is located, in that a filter unit is located in the housing, through which the fluid flows. In this way, the pressure transducer and the particle filter are integrated into one component with a common housing. This makes possible a lower-cost production, because, in comparison to the systems of the state of the art, in which the pressure transducer and the particle filter are designed as separate components and are located in the injection hose, one behind the other, one of the housing parts is omitted. Also, the installation of the injection is made easier by the use of the pressure measurement cell, in accordance with the disclosure, since only the pressure measurement cell with the integrated filter unit has to be inserted, in one operation, into the injection house, whereas, with known systems, the pressure sensor and the particle filter have to be inserted one after the other. Furthermore, a simple handling is guaranteed when inserting the hose system into a hose pump, since there is now only one housing part contained in the hose system, in which both the filter unit as well as the pressure transducer are kept.

The filter unit is preferably designed as an elongated filter cartridge with a cartridge housing and a filter sieve, which can be stuck into a housing borehole, wherein the cartridge housing carries a filter sieve and has a cartridge opening, through which the fluid under pressure flows into the filter cartridge. In this way, the flow cross section through the filter unit can be increased, in comparison to the known particle filters, in which the flow cross section corresponds to the cross section of the injection hose, because the effective filter area of the elongated filter cartridge can be designed larger than the hose cross section. The pressure decline produced in the filter unit is minimized in this manner and the pressure stability is improved.

In a preferred embodiment example of the pressure measurement cell, in accordance with the disclosure, the filter unit is located in a housing borehole in the housing, wherein, between the inside surface of the housing borehole and the outside of the filter cartridge, a chamber connected with an outlet opening of the housing is formed, into which the fluid from the filter unit flows. Appropriately, recesses covered by the filter sieve are formed in the cartridge housing; by means of these recesses, the fluid flows out from the filter unit. The filter sieve is appropriately made from a filter fabric with a mesh width of 10-15 µm and, depending on the application purpose, is, as a function of the fluid to be injected, hydrophilic or hydrophobic.

The filter cartridge is preferably formed in such a way that the flow density of the fluid flowing out of the filter unit into the chamber is essentially constant along the filter cartridge over its entire length. To this end, flow canals that appropriately run in the cartridge housing in the longitudinal direction of the filter cartridge are formed; the fluid is conducted in them, wherein the flow canals are limited, on the one hand, by the outside area of the cartridge housing and, on the other hand, by the filter sieve. A flow density of the flowing-out fluid, which is constant over the entire length of the filter cartridge in the direction of flow, can be thereby attained in that the flow cross section of the flow canals are continuously reduced in the direction of flow.

The pressure transducer is expediently coupled with a pressure sensor, for example, a piezoresistive or piezoelectric pressure sensor.

The filter unit is preferably secured by a stopper which can be pushed into a front-side inlet opening of the housing, or by a socket in the housing. The stopper or the socket has a tube-like connecting piece for a hose line of the infusion or injection system and a passage canal, through which the fluid is conducted into the filter unit. In an appropriate embodiment example, the filter unit is situated in the housing borehole so that it can be replaced.

Expediently, the filter unit and the inside areas of the housing borehole have guide means, corresponding to one another, such as guide grooves and guide ribs, via which the filter cartridges are guided into the housing borehole, when inserted into the housing, or when replaced with a new filter unit, can be pulled from the housing. In this way, tilting or jamming can be prevented when the filter unit is pulled out or pushed in.

BRIEF DESCRIPTION OF THE DRAWINGS

These and other advantages of the disclosure can be deduced from the embodiment example described, in more detail, below, with reference to the accompanying drawings. The drawings show the following.

DETAILED DESCRIPTION OF THE DISCLOSURE

FIGS. 1 to 5 show a pressure measurement cell in accordance with the disclosure in a perspective view. This pressure measurement cell is used in an infusion or injection system for the injection of a fluid, for example, for the intravenous injection of a contrasting agent. The pressure measurement cell has (its own) housing 1, which is appropriately designed as a plastic injection molding. The housing has a housing borehole 1c with an inlet opening 2a on its front end and an outlet opening 2b on its rear end 1b. The rear end 1b of the housing 1 is made in the shape of a tube and is used to connect a hose line of an injection housing of the infusion or injection system. The front end 1a of the housing 1 is also designed in the shape of a tube with an oval tube cross section.

At least one pressure transducer 3 and at least one filter unit 4 are located in the housing 1. The pressure transducer 3 is preferably a membrane 10, for example, a silicone membrane. In the embodiment example shown here, two such pressure transducers 3, in the form of membranes 10, are provided, which are located in membrane openings 15 of the wall of the housing 1. These membrane openings 15 are thereby in two plate-shaped housing parts 16 and 17 of the housing 1 on its upper side and are connected with the housing borehole 1c (FIG. 4).

Figure 1:
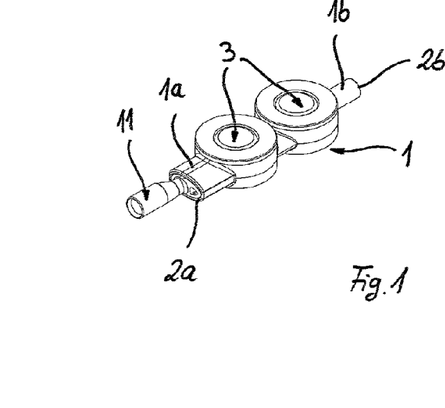
FIG. 1 Perspective representation of a pressure measurement cell in accordance with the disclosure.
Figures 2, 4:
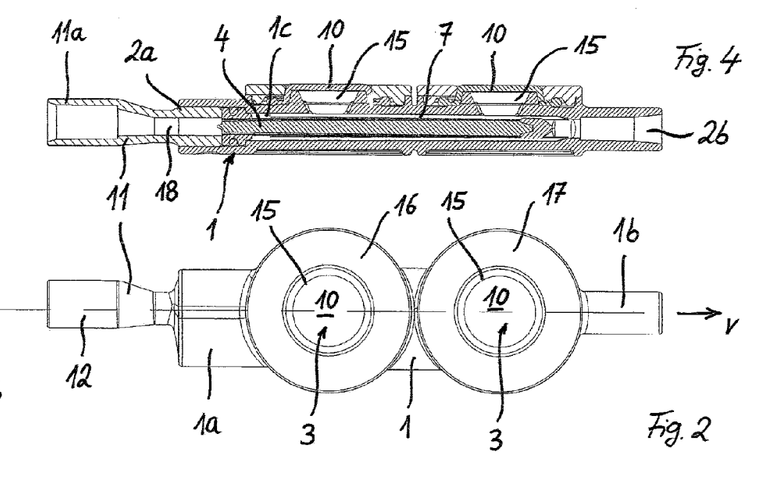
FIG. 2 top view of the pressure measurement cell of FIG. 1.
FIG. 4 cross section through the pressure measurement cell of FIG. 3, along the O-O plane.
Figure 3:
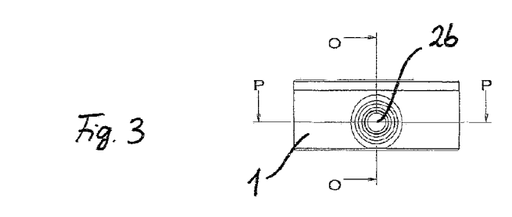
FIG. 3 side view of the rear front side of the pressure measurement cell of FIG. 2.
Figure 5:
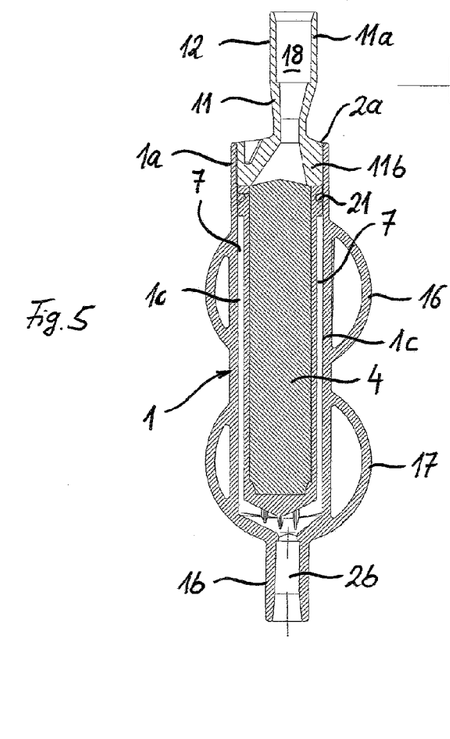
FIG. 5 cross section through the pressure measurement cell of FIG. 3, along the P-P plane.
Figure 6:
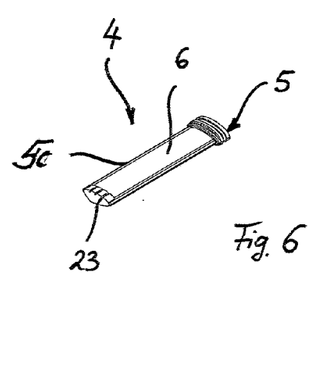
FIG. 6 perspective representation of the filter unit of the pressure measurement cell of FIG. 1.
Figure 7:
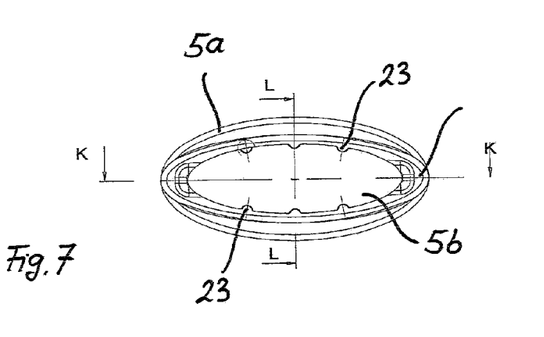
FIG. 7 side view of the front area of the filter unit of FIG. 6.
Figure 8:
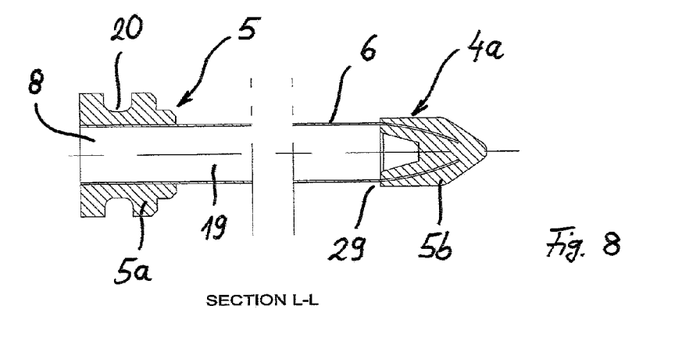
FIG. 8 cross section through the filter unit of FIG. 7, along the L-L plane.
Figure 9:
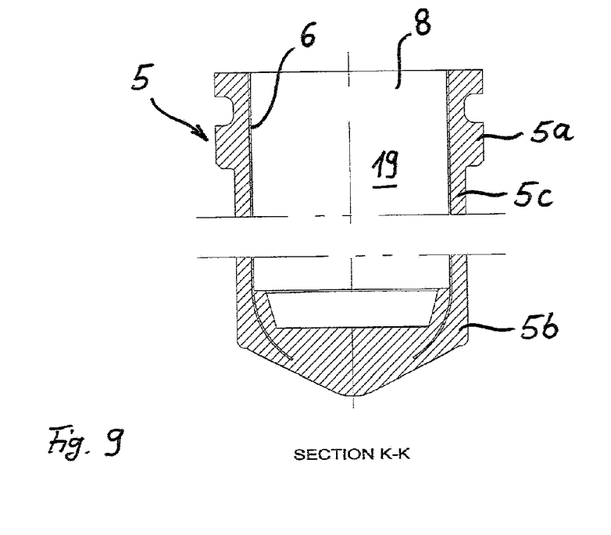
FIG. 9 cross section through the filter unit of FIG. 7, along the K-K plane.
Figure 10:
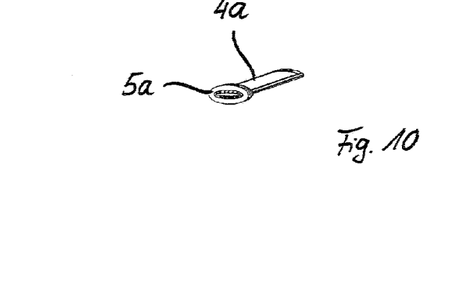
FIG. 10 perspective representation of a second embodiment of a filter unit for a pressure measurement cell in accordance with the disclosure.
Figures 11, 13:
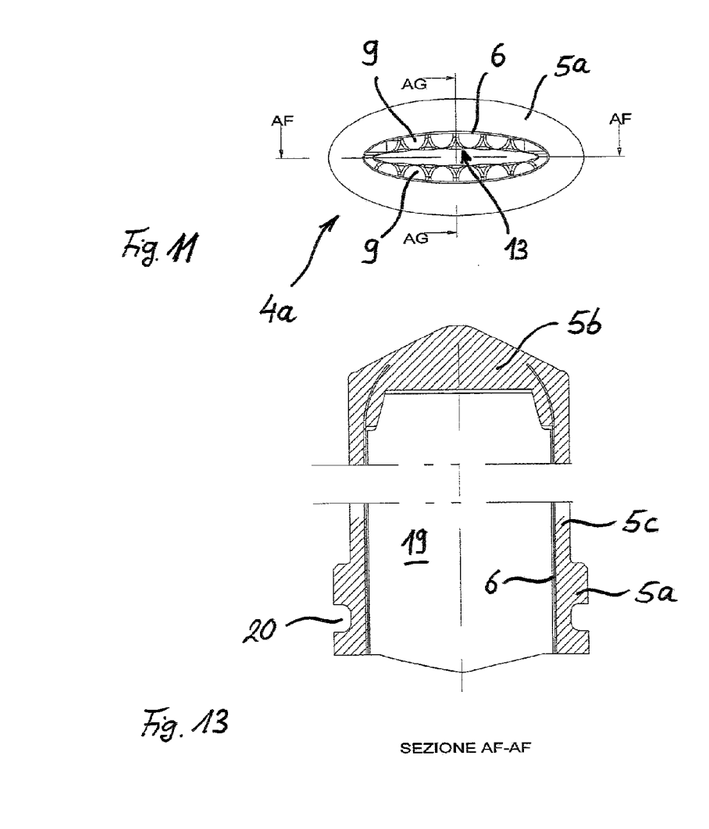
FIG. 11 side view of the front surface of the filter unit of FIG. 10.
FIG. 13 cross sectional representation of the filter unit of FIG. 11, along the AF-AF plane.
Figure 12:
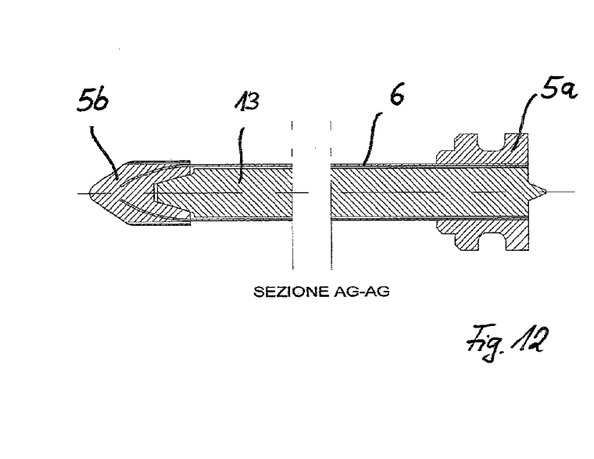
FIG. 12 sectional representation of filter unit of FIG. 11, along the AG-AG plane.
Figure 14:
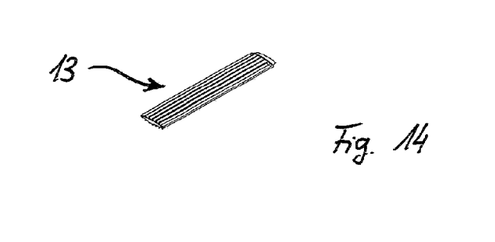
FIG. 14 perspective representation of a use of a third embodiment of a filter unit for a pressure measurement cell in accordance with the disclosure.
Figure 15:
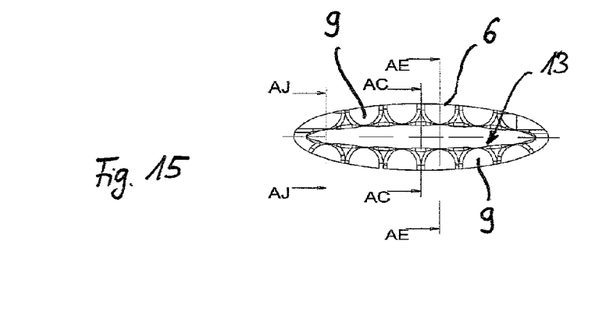
FIG. 15 side view of the front area of the use of FIG. 14.
Figures 16, 17:
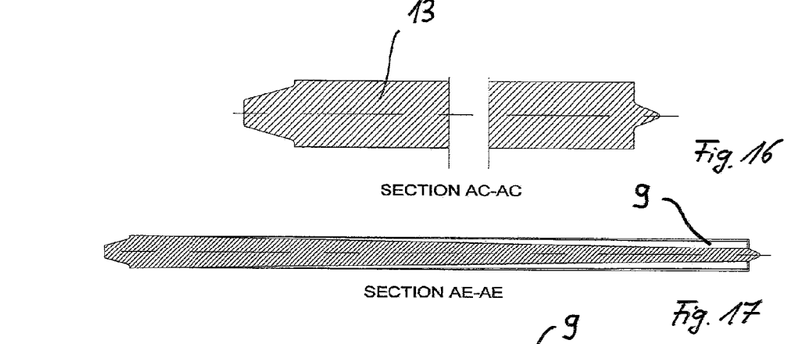
FIG. 16 sectional representation of the use of FIG. 15, along the AC-AC plane.
FIG. 17 sectional representation of the use of FIG. 15, along the AE-AE plane.
Figure 18:
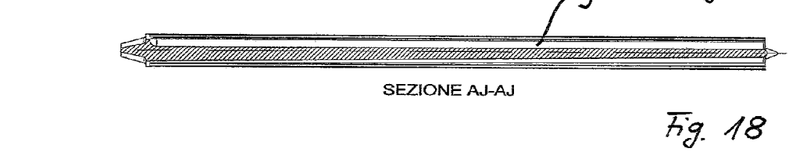
FIG. 18 sectional representation of the use of FIG. 15, along the AJ-AJ plane.
Figure 19:
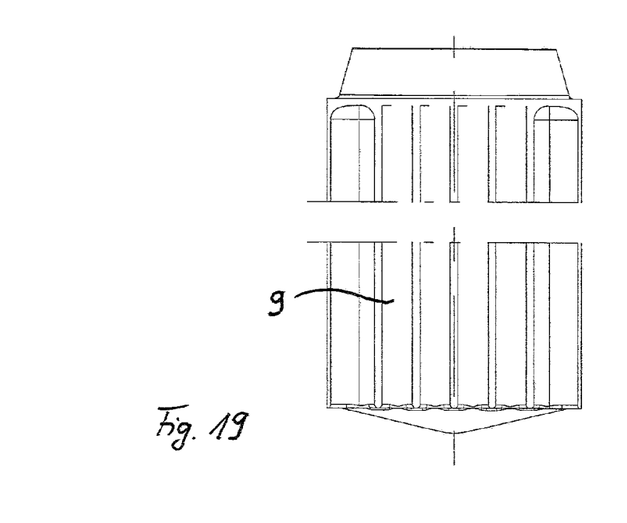
FIG. 19 top view of the use of FIG. 14.
Figure 20:
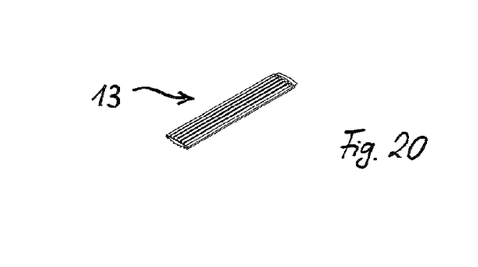
FIG. 20 perspective representation of a use for a fourth embodiment of a filter unit for a pressure measurement cell in accordance with the disclosure.
Figure 21:
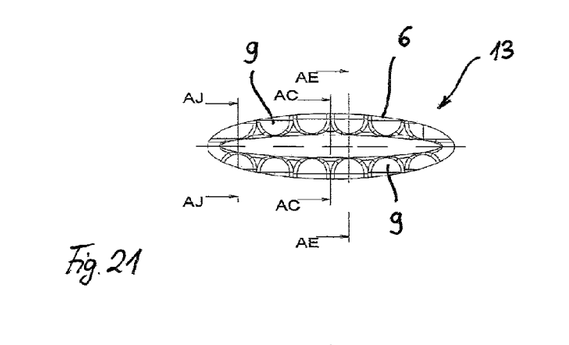
FIG. 21 side view of the front area of the use of FIG. 20.
Figure 22:
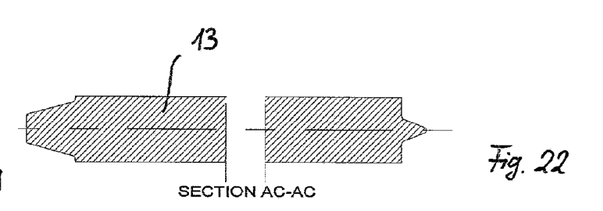
FIG. 22 sectional representation of the use of FIG. 21, along the AC-AC plane.
Figure 23:
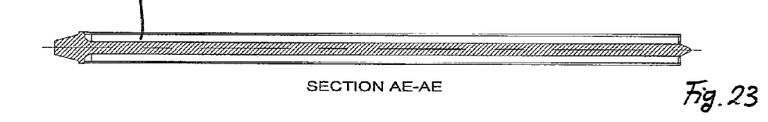
FIG. 23 sectional representation of the use of FIG. 21, along the AE-AE plane.
Figure 24:
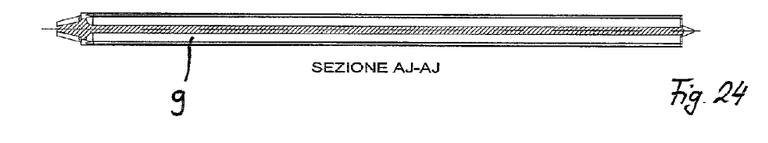
FIG. 24 sectional representation of the use of FIG. 21, along the AJ-AJ plane.
Figure 25:
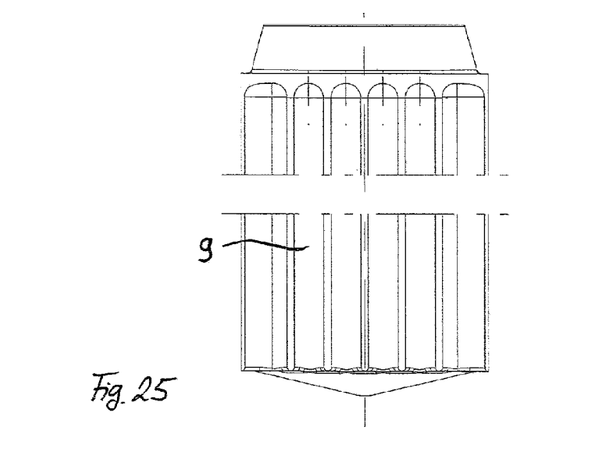
FIG. 25 top view of the use of the filter unit of FIG. 20.

The filter unit 4, situated in the housing borehole 1c, can be seen in the sectional representations of FIGS. 4 and 5 and is shown, in detail, in FIGS. 6-9. The filter unit 4 is located in the housing borehole 1c and is affixed there by means of a removable stopper 11 and secured against slipping out. The stopper 11 has a passage borehole 18 and a front end 11a and a rear end 11b (FIG. 5). The front end 11a of the stopper 11 is designed as a tube shaped connecting piece 12 for the connection with a hose line of the infusion or injection system. The rear end 11b of the stopper 11 is shaped in a complementary manner to the oval shape of the front end 1a of the housing 1 and protrudes into the inlet opening 2a of the housing 1. The rear end 11b of the stopper 11 is appropriately clamped there to secure the filter unit 4 or locked by means of a locking element.

The filter unit 4 can be fastened either in the housing borehole 1c, for example, by cementing, or it can be arranged therein so it can be replaced. A replaceable arrangement makes possible a change of a used-up filter unit, if it should become clogged. To change a spent filter unit 4, the stopper 11 can be pulled out of the housing opening 2a, so as to free the access to the filter unit 4, which can then be pulled out of the housing borehole 1c and can be replaced with a new filter unit.

The filter unit 4, shown in FIG. 6-9, is designed as an elongated filter cartridge 4a with a hollow cartridge housing 5 and a filter sieve 6. The cartridge housing 5 has a front section 5a, a rear section 5b, and a longitudinal section 5c that connects the front section 5a and the rear section 5b. The longitudinal section 5c is thereby formed by at least two braces 5c that extend in the longitudinal direction of the filter cartridge 4, which are appropriately connected, in one piece, as a plastic injection molding, with the front section 5a and the rear section 5b of the cartridge housing 5. The cartridge housing 5 has recesses in the middle section, which are covered by the filter sieve 6.

The filter sieve 6 is preferably a filter fabric with a mesh width of 10-15 μm. The filter sieve 6 is appropriately cast with the cartridge housing 5 in the front section 5a, in the rear section 5b, and in the middle section 5c and is thus carried by the cartridge housing 5. A cartridge opening 8 is provided in the front section 5a, which is connected with the interior 19 of the hollow cartridge housing 5. If the filter unit 4 is inserted into the interior of the housing 1 of the pressure measurement cell, as is shown, for example, in FIG. 5, the cartridge opening 8 is connected with the borehole 18 of the stopper 11. In this way, a fluid that is to be injected, which is conducted, via an injection hose, to the stopper 11 connected thereon, can flow in through the borehole 18 in the stopper 11 and through the cartridge opening 8 into the interior 19 of the filter cartridge 4a and flow out, from there, through the filter sieve 6.

The filter unit 4 with the elongated filter cartridge 4a is pushed forward into the interior of the housing 1 with the rear section 5b of the cartridge housing 5 and there affixed by means of the stopper 11, as shown in FIG. 5. The front section 5a of the cartridge housing 5 has a protruding flange with an annular groove 20 on its outside circumference. An O-ring 21 is placed into this annular groove 20 for sealing. The outside diameter of the flange-shaped section 5a of the cartridge housing 5 thereby corresponds to the inside diameter of the housing borehole 1c, into which the filter unit 4 is inserted. The diameter of the middle section 5c and the rear section 5b of the filter cartridge 4a is smaller than the outside diameter of the front section 5a or the inside diameter of the housing borehole 1c, so that a chamber 7 is formed between the outside area of the filter cartridge 4a in the middle section 5c and in the rear section 5b as well as the inside area of the housing borehole 1c. The fluid flowing out of the interior 19 of the filter cartridge 4a flows into this chamber 7. The chamber 7 is in contact, via the membrane openings 15, with the membranes 10 of the pressure transducer 3. The pressure of the fluid, which flows into the chamber 7 through the filter unit, is thus transferred to the membrane 10 of the pressure transducers 3. The pressure transducers 3 are coupled with a nondepicted pressure sensor, which detects the deformation of the membrane 10, dependent on the fluid pressure, and determines the fluid pressure therefrom. The pressure sensor can thus detect the pressure of the fluid and display it by means of a nondepicted display unit.

Figure 26:
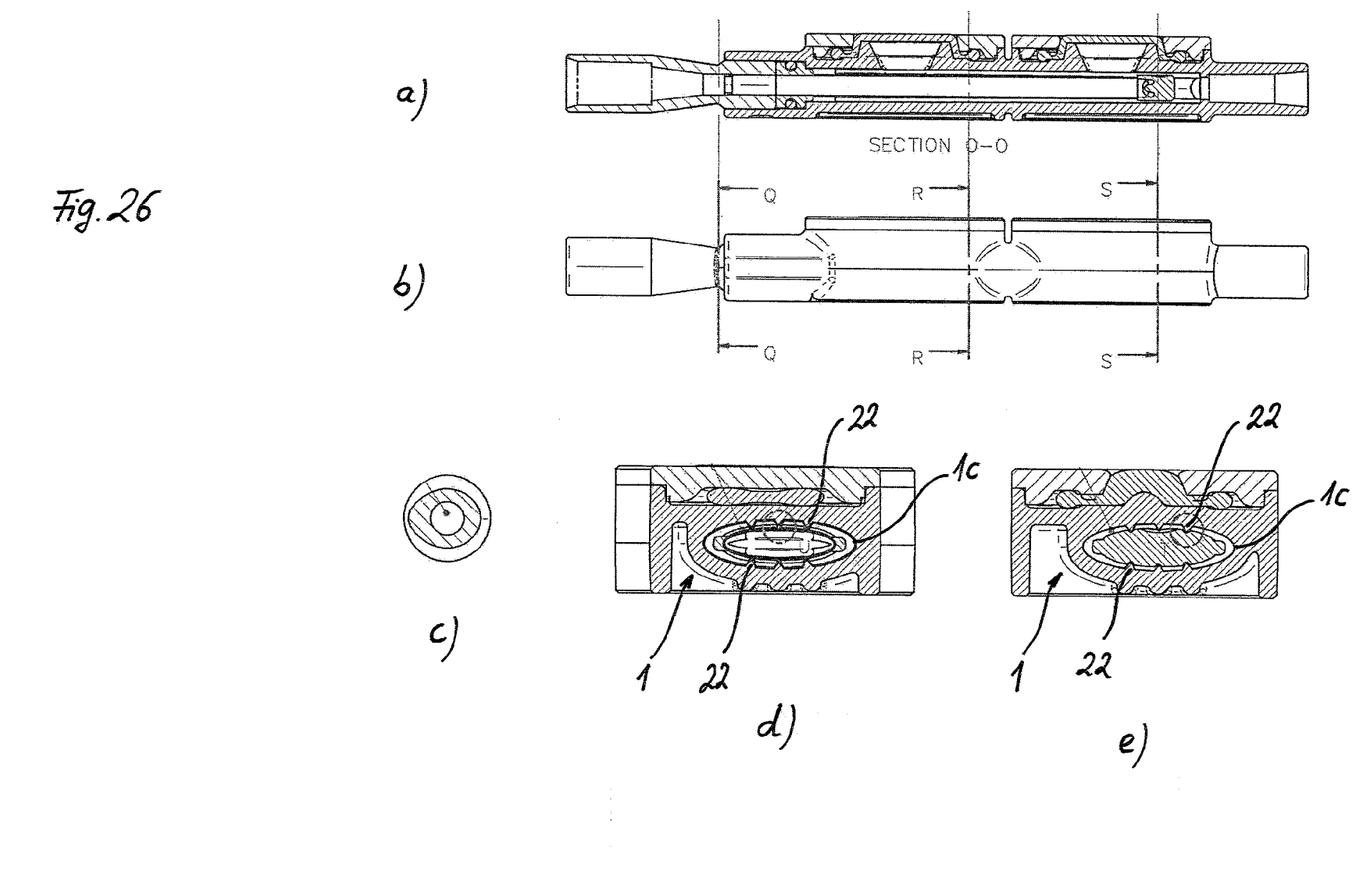
FIG. 26 representation of another embodiment example of a pressure measurement cell in accordance with the disclosure in a cross-sectional representation (FIG. 26a), a top view (FIG. 26b), and sectional representations along the Q-Q plane (FIG. 26c), the R-R plane (FIG. 26d), and the S-S plane (FIG. 26e).

FIG. 26 shows another embodiment example of a pressure measurement cell, in accordance with the disclosure, which essentially corresponds to the embodiment example of FIGS. 1-5. From the sectional representations of FIGS. 26d and 26e, one can see that the inside area of the housing borehole 1c has crosslinks 22, protruding, in a zigzag manner, on its upper side and its underside. These zigzag crosslinks 22 protrude into the interior of the housing borehole 1c and essentially extend over the entire length of the housing 1. Grooves 23, corresponding, in an appropriate number and in appropriate places, with these crosslinks 22, are provided on the rear section 5b of the cartridge housing 5. These grooves 23 can be seen in the representation of FIG. 6 and FIG. 7. When the filter unit 4 is pushed into the housing borehole 1c, the zigzag crosslinks 22 mesh into the corresponding grooves 23 on the cartridge housing 5. Thus, when the filter unit 4 is pushed into the housing borehole 1c, a secure guidance and a perfectly fitting seat for the filter cartridge 4a in the housing 1 are guaranteed.

FIGS. 10-13 show a second embodiment of a filter unit 4 for use in the pressure measurement cell in accordance with the disclosure. This essentially corresponds to the filter unit of the embodiment example of FIGS. 6 to 9, and for this reason, corresponding parts are designated with the same reference symbols. Supplementary to the embodiment example of FIGS. 6 to 9, the filter unit 4 of the embodiment example of FIGS. 10 to 13 has an insert 13 which is shoved into the interior 19 of the cartridge housing 5. As can be seen from the representation of FIG. 11, the insert 13 has flow canals 9 that are located, next to one another, on its outside circumference and extend in the longitudinal direction of the insert 13. The flow canals 9 are thereby limited, on the one hand, by the outside area of the insert 13, provided with semi-tubular incisions and, on the other hand, by the filter sieve 6, placed thereon. The fluid flowing into the filter cartridge 4a, flows, through the flow canals 9, in the longitudinal direction of the filter cartridge 4a and, from there, through the filter sieve 6, from the filter cartridge 4a and into the chamber 7.

In a modified embodiment example of the insert, which is shown in FIGS. 14-19, the flow canals 9 are formed in such a way that their flow cross section is continually reduced in the flow direction. This can be seen, in particular, in FIGS. 17 and 18. By the formation of the flow canals, it is possible for the flow density of the fluid flowing from the filter unit 4 into the chamber 7 to be at least essentially constant over the entire length of the filter cartridge 4a.

In the other embodiment example of an insert 13, which is shown in FIGS. 14-19, the flow canals 9 are, on the other hand, formed with a constant flow cross section over the entire length of the insert 13. In this embodiment example, the flow density of the fluid flowing from the filter unit 4 is smaller in the upward flow (rear) area than in the downward flow (front) area.

The invention claimed is:

1. A combined filter and pressure measurement cell device for use in an infusion or injection system for the injection of a fluid under pressure, the device comprising:
   a housing forming an elongated inner bore defining a longitudinal axis, the bore having an inner surface, the housing having an inlet and an outlet;
   at least one elongate filter unit including
      a filter carrier sized and dimensioned to extend within the inner bore along the longitudinal axis, and
      a filter sieve having an unfiltered input side and filtered output side, the filter sieve supported by the filter carrier and having a longitudinal axis extending along the longitudinal axis of the housing;
   at least one pressure transducer connected to the housing, for the detection of the pressure of the fluid;
   a chamber formed along the longitudinal axis of the housing between the output side of the filter sieve and the inner surface of the bore, the at least one pressure sensor in fluid communication with the chamber and positioned to contact pressurized fluid that has passed through the filter sieve and into the chamber.

2. The device of claim 1, wherein the filter sieve is formed from a filter fabric with a mesh width of 10-15 μm, wherein the filter fabric is hydrophilic or hydrophobic.

3. The device of claim 1, wherein the diameter of the filter sieve changes along the longitudinal axis to thereby control the flow volume along the length of the filter cartridge.

4. The device of claim 1, the filter carrier further including longitudinally extending flow canals formed in an interior of the filter carrier adjacent the filter sieve.

5. The device of claim 1, wherein the filter carrier is sized and dimensioned to be releaseably inserted into the housing along the longitudinal axis, the filter carrier further including a plurality of flow canals forming an exterior portion of the filter carrier, the flow canals covered by the filter sieve.

6. The device of claim 4, wherein the flow cross section of the flow canals is continually reduced along the longitudinal axis in a direction away from the housing inlet.

7. The device of claim 1, wherein the at least one pressure transducer includes a membrane, on which the pressure of the fluid acts.

8. The device of claim 1, wherein the at least one pressure transducer includes a pressure sensor selected from a piezoresistive pressure sensor and a piezoelectric pressure sensor.

9. The device of claim 1, the filter unit further including a stopper which forms a seal, the stopper pushable into the inlet and including a hose connector in fluid communication with a borehole opening into an interior of the filter carrier.

10. The device of claim 1, wherein the filter frame and the housing form mateable crosslinks and grooves which guide insertion of the filter carrier.

11. The device of claim 1, wherein the filter unit is removably insertable into the inner bore.

12. A device for filtering and measuring pressure of a fluid for the therapeutic treatment of a patient, comprising:
 a housing forming an elongated inner bore defining a longitudinal axis, the bore having an inner surface, the housing having an inlet and an outlet;
 at least one elongate filter unit including
  a filter carrier sized and dimensioned to extend within the inner bore along the longitudinal axis, and
  a filter material supported by the filter carrier and having a longitudinal axis extending along the longitudinal axis of the housing to define a filtering area having a cross-section substantially larger than the housing inlet, the filter material having a mesh width selected to filter materials from the fluid as the fluid passes through the filter area from an unfiltered input side to a filtered output side, the filter carrier defining a flow path of the fluid under pressure from an inlet into the filter carrier and through the filtering area;
 at least one pressure detecting transducer positioned upon the housing and including a membrane opening formed through the bore of the housing adjacent the filtering area;
 a chamber formed along the longitudinal axis of the housing between the output side of the filter material and the inner surface of the bore, the at least one pressure sensor in fluid communication with the chamber and positioned to contact pressurized fluid that has passed through the filter material and into the chamber.

13. The device of claim 12, the inlet sized and dimensioned to form a post upon which medical tubing carrying the fluid to be filtered and measured can be mounted.

14. The device of claim 12, the transducer integrally formed in part with the housing.

15. The device of claim 12, wherein a diameter of the filter carrier changes along the longitudinal axis to adjust fluid pressure through the filter material along the longitudinal axis.

16. The device of claim 12, the filter carrier removably insertable into the housing inner bore.

17. The device of claim 16, the filter carrier including longitudinally shapes mateable with longitudinally extending shapes within the housing inner bore to thereby orient the filter carrier with respect to the housing when the filter carrier is inserted into the housing inner bore.

18. The device of claim 12, the filter carrier including grooves which extend along the direction of the longitudinal axis and which conduct fluid from an area proximate the housing inlet to an area proximate a side of the housing opposite to the housing inlet, the grooves covered by the filter material.

19. The device of claim 12, wherein a sidewall of the at least one transducer is integrally formed from material of the housing.

20. The device of claim 12, wherein the at least one transducer forms a disc shape and is arranged along the longitudinal axis of the housing.

* * * * *